United States Patent [19]

Huang

[11] Patent Number: 4,588,737
[45] Date of Patent: May 13, 1986

[54] ANTIALLERGIC BIS-IMIDAZOLINOAMINO DERIVATIVES

[75] Inventor: Fu-chih Huang, Leonia, N.J.

[73] Assignee: USV Pharmaceutical Corp., Tarrytown, N.Y.

[21] Appl. No.: 684,214

[22] Filed: Dec. 20, 1984

[51] Int. Cl.$^4$ .................. A61K 31/415; C07D 233/50
[52] U.S. Cl. .................................. 514/392; 514/402; 548/316; 548/350
[58] Field of Search ............... 548/316, 350; 514/392, 514/402

[56] References Cited

U.S. PATENT DOCUMENTS

| | | | |
|---|---|---|---|
| 2,461,156 | 2/1949 | Hartmann et al. | 548/316 |
| 3,905,992 | 9/1975 | Wittekind et al. | 548/316 |
| 4,389,403 | 7/1983 | May et al. | 548/316 |

*Primary Examiner*—Richard A. Schwartz
*Assistant Examiner*—Kurt G. Briscoe

[57] ABSTRACT

Compounds possessing valuable therapeutic activity particularly as lipoxygenase inhibitors possessing anti-inflammatory and anti-allergic properties, of the formula:

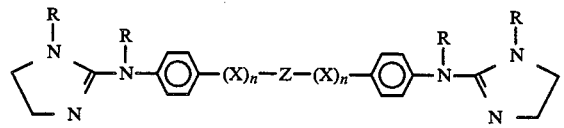

wherein

Z is an unsubstituted normal alkylene chain of up to 8 carbon atoms or a substituted normal alkylene chain in which the substituent is lower alkyl, phenyl or benzyl containing up to 8 carbon atoms in the normal chain and up to a total of about 12 carbon atoms;

X=O to S;

n=0 or 1; and each R is H, lower alkyl or lower alkanoyl; and salts thereof, especially pharmaceutically-acceptable salts.

13 Claims, No Drawings

ANTIALLERGIC BIS-IMIDAZOLINOAMINO DERIVATIVES

This invention relates to new chemical compounds which possess valuable therapeutic activity particularly as lipoxygenase inhibitors possessing anti-inflammatory and antiallergic properties.

U.S. Pat. Nos. 4,327,102 and 4,394,509 describe sulfoxides of the formula:

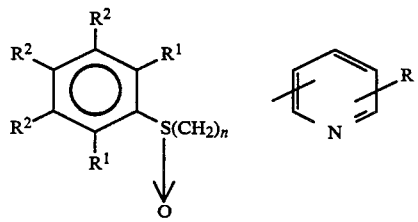

in which R is hydrogen or a hydrocarbon radical, $R^1$ is H or F, $R^2$ is H, F, Cl or $CF_3$, and n is 1 or 2, as anti-ulcer and/or anti-secretory compounds, as well as the corresponding thioether compounds from which prepared by oxidation of the thioether sulfur to the sulfone. The thioethers of the said structure are also described in U.S. Pat. Nos. 4,415,579; 4,394,509 and 4,337,259 as anti-ulcer compounds.

I. Eur. J. Med. Chem.-Chem. Ther.-1983-18 (pp. 277-285), described compounds of the following structures as anti-secretory agents:

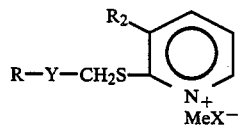

R=various heterocyclics, cyclohexyl, various substituted phenyls;
Y=$CH_2$, S, $(CH_2)_2$, $(CH_2)_3$, CHMe, C=O, C=C;
$R_2$=H, CHO, $CH(OEt)_2$

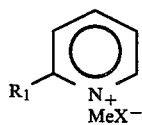

$R_1$ is benzyloxypyridyl quaternary salts, phenylthiomethyl, benzylsulfoxy, benzylthio, etc.

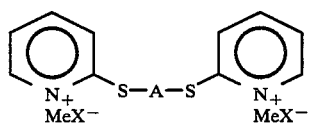

A=alkylene up to $C_5$, and

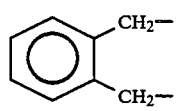

-continued
$R_1CH_2SR_2$
|
X $R_1$ and $R_2$=various heterocycles, phenyl, substituted phenyl
X=—, O, or $O_2$.

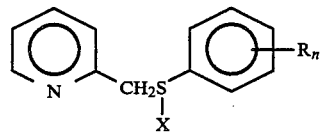

$R_n$=H, halogen, or methoxy.

The present new compounds are of the formula:

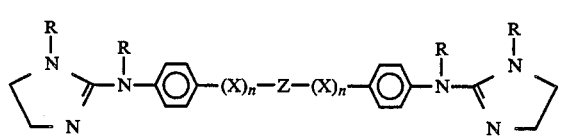

and salts thereof;
wherein:

Z is an unsubstituted normal alkylene chain of up to 8 carbon atoms or a substituted normal alkylene chain in which the substituent is lower alkyl, phenyl or benzyl containing up to 8 carbon atoms in the normal chain and up to a total of about 12 carbon atoms;

X=O or S;

n=0 or 1; and each R is H, lower alkyl or lower alkanoyl.

The preferred compounds are those in which the alkylene chain represented by Z contains from 4 to 6 carbon atoms and is a normal alkylene chain, most preferably, unsubstituted. Of the substituents on Z, the preferred are lower alkyl, e.g., methyl, ethyl and isopropyl.

Further preference exists for compounds in which X's and n's are the same, X is O, n is 1, and the R groups are H or acetyl.

Additional variations in the structural formula representing the instant compounds can be effected without significantly altering the therapeutic properties, e.g., lipoxygenase inhibition. For example, the phenyl groups separated by $—(X)_n—Z—(X)_n—$ can be substituted by one or more of a variety of substituents such as alkyl, aryl, halogen, hydroxy, alkoxy, phenoxy, benzyloxy, alkylthio, carboxy, carbalkoxy, carboxamide, nitrilo, sulfamyl, amino, alkylamino, dialkylamino, formyl, trihalomethyl, and nitro groups. The imidazoline moieties may be replaced by other heterocyclic moieties such as those containing at least one oxygen, sulfur or nitrogen and include the so-called benzoheterocyclic rings. Exemplary heterocyclics include thiophene, pyrrole, pyridine, thiophene, thiazole, piperazine, oxazole, benzofuran, quinoline, indole, benzothiophene, benzoxazole and similar heterocyclic rings as well as the N-oxides of the nitrogen heterocyclics.

The alkyl groups, either alone or within the various substituents defined hereinbefore are preferably lower alkyl which may be straight or branched-chain, and include methyl, ethyl, propyl, isopropyl, butyl, isobutyl, amyl, hexyl and the like.

The halo atoms in halo and trihalomethyl are Cl, Br, I and preferably F. The aryl groups are preferably phenyl or naphthyl.

The present new compounds are prepared by known methods from starting materials either known or readily preparable.

The following general procedure can be employed.

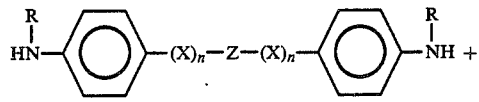

II

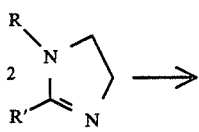

III
R' = leaving group, e.g., SCH$_3$, Cl, Br, etc.

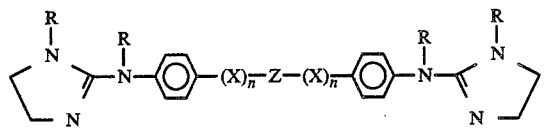

The substituents are as previously defined.

The synthetic procedure is predicated on removal of the reactive hydrogen on position-2 of the imidazoline reactant with formation of a bond with each of the amino groups of the phenyl rings. This condensation can be effected in the presence of a variety of compounds known for this purpose, e.g., phosphorus oxychloride, thionyl chloride and like compounds. In a preferred mode, it is advantageous to block the secondary amino nitrogen of the imidazoline ring to avoid secondary or competing reactions, particularly when phosphorus oxychloride or thionyl chloride is used. Any blocking group can be employed for this purpose, the preferred being groups which are readily hydrolyzable such as lower alkanoyl groups, e.g., acetyl, propionyl, butynyl and the like. Of course, where R in the imidazoline moiety is to be other than H, e.g., alkyl, alkanoyl, etc., no blocking is required.

A further preparative procedure involves the use of an imidazoline substituted in the 2-position with a leaving group which combines with a hydrogen of the amino nitrogen of the formula II compound. Such leaving groups are well known in the art and preference residues in the use of such leaving groups which combine with the aforesaid hydrogen to form compounds which are substantially unreactive with the reactants and products under the preparative experimental conditions.

The aforesaid reactions can be carried out at room temperature or at elevated temperatures up to the reflux temperature of the reaction mixture. The use of temperatures higher than room temperature usually will merely shorten the reaction time which can be determined by monitoring the reaction mixture periodically using known techniques, e.g, chromatogrphic techniques. Usually the reactions are effected in a solvent for efficiency of reaction as is commonly appreciated by those in the art. Solvents are not always required, since liquid reactants, e.g., POCl$_3$ or SO$_2$Cl$_2$, can serve as solvents as well.

The products are obtained by classical methods of recovery from the reaction mixture.

It is possible to effect further reactions on the formed products such as introduction of alkyl or alkanoyl groups on available positions of the amino nitrogens in the product using known methods such as alkylating or acylating reactions.

The starting compounds for production of the present new compounds are either known or readily preparable as illustrated in the examples which are included herein.

The present new compounds contain basic nitrogen and can form salts with acids. All such acid salts are contemplated by the invention but especially preferred are salts with pharmaceutically acceptable acids, such as hydrochloric, sulfuric, nitric, toluenesulfonic, acetic, propionic, tartaric, malic and similar such acids well known in this art. In addition, quaternary salts can be formed using standard techniques of alkylation employing, for example, hydrocarbyl halides or sulfates such as methyl, ethyl, benzyl, propyl or allyl halides or sulfates.

The compounds of the present invention can be administered to the host in a variety of forms adapted to the chosen route of administration, i.e., orally, intravenously, intramuscularly or subcutaneous routes.

The active compound may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of the unit. The amount of active compound in such therapeutically useful compositions is such that a suitable dosage will be obtained. Preferred compositions or preparations according to the present invention are prepared so that an oral dosage unit form contains between about 50 and 300 mg of active compound.

The tablets, troches, pills, capsules and the like may also contain the following: A binder such as gum tragacanth, acacia, corn starch or gelatin; excipients such as dicalcium phosphate, disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

The active compound may also be administered parenterally or intraperitoneally. Solutions of the active compound as a free base or pharmacologically acceptable salt can be prepared in water suitably mixed with a surfactant such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the free-drying technique which yield a powder of the active ingredient plus any additional desired ingredient from previously sterile-filtered solution thereof.

The following examples further illustrate the invention.

EXAMPLE 1

1,6-Bis(p-nitrophenyl)-1,5-hexadiene

To a solution of 0.76 g of sodium in 50 ml of absolute EtOH was added 12.25 g of butane-1,4-bis-triphenyl phosphonium bromide. Ten minutes later, 5 g of p-nitrobenzaldehyde was then added. The reaction mixture was stirred at room temperature overnight and the solvent was removed in vacuo. The residue was treated with $CH_2Cl_2$. The organic solution was washed with $H_2O$, dried with ($MgSO_4$), and concentrated to give 0.5 g of product as a yellow solid.

EXAMPLE 2

1,6-Bis-(p-aminophenyl)hexane

A mixture of 0.49 g of the Example 1 product and 0.2 g of 5% Pd/C in 50 ml of EtOH was hydrogenated at 45 psi for 3 hours. After filtration (Celite), the filtrate was concentrated to give 0.2 g of product as a white solid.

EXAMPLE 3

1,6-Bis[N-[2-(1-acetyl)imidazolino]-4-aminophenyl]hexane or
1,6-bis(4-(N-(2-(1-acetyl)imidazolino)amino)phenyl)-hexane A solution of 0.2 g of the Example 2 product and 0.19 g of N-acetyl 2-imidazolone in 10 ml of $POCl_3$ was heated at 50° C. for 2 days. Most $POCl_3$ was removed in vacuo and the residue was treated with $H_2O$. The aqueous solution was basified and extracted with $CH_2Cl_2$. The organic solution was separated, dried and concentrated. The crude product, after column chromatography purification gave 0.2 g of product as a white solid.

EXAMPLE 4

1,6-Bis[N-(2-imidazolino)-4-aminophenyl]hexane or
1,6-bis(4-(N-(2-imidazolino)amino)phenyl)hexane A solution of 0.3 g of the Example 3 product in 20 ml of 25% NaOH and 10 ml dioxane was heated at 60° C. overnight. The aqueous solution was acidified to pH 2 and was extracted with ether. The aqueous solution was then rebasified with 1N NaOH to pH 8. The precipitated product was collected on a filter to give 0.2 g of product as an off-white powder, m.p. 181°–183° C.

EXAMPLE 5

1,4-Bis-(4-nitrophenoxy)-2-butene

A mixture of 5.6 g of p-nitrophenol, 4.3 g of 1,4-dibromo-2-butene, and 5.6 g of $K_2CO_3$ in 80 ml of acetone was heated at 60° C. overnight. The reaction mixture was poured into water and filtered to give, after drying, 6.8 g of product as a creamy colored solid.

EXAMPLE 6

1,4-Bis-(4-aminophenoxy)-2-butene

The Example 5 product (6 g) and 1 g of 5% Pd/C in 150 ml of EtOH was hydrogenated at 30 psi overnight and the reaction mixture then filtered. The solid compound and catalyst were boiled with EtOH, filtered, and the ethanolic solution was evaporated to give 1.5 g of a white solid.

EXAMPLE 7

1,4-Bis-[4-(N-(2-imidazolino)amino)phenoxy]butane-hydrogen iodide salt

A solution of 2 g of the Example 6 product and 4.48 g of 2-methylthioimidazoline.HI in 20 ml of pyridine was heated to reflux for 2 hours. After standing at room temperature overnight, pyridine was removed under vacuo. The residue was washed successively with ether and $CH_2Cl_2$ until a creamy solid powder was obtained. Filtration gave 4.3 g of product; m.p. 130° C. (dec.).

In a similar fashion according to the procedures of the preceding examples, the following compounds can be prepared from appropriate starting materials:
1,4-Bis-(4-(N-(2-imidazolino)amino)phenyl)-2,3-dimethylbutane;

1,6-Bis-(3-methyl-4-(N-(2-imidazolino)amino)phenyl)-hexane;
1,6-Bis(3-chloro-4-(N-(2-imidazolino)amino)phenyl)-hexane;
1,5-Bis(4-(N-(2-imidazolino)amino)phenyl)pentane;
1,5-Bis(4-(N-(2-imidazolino)amino)phenyl)-3-benzylpentane;
1,6-Bis(2-(N-(2-imidazolino)amino)phenyl)hexane.

The compounds of the present invention have potent activity in regulating the formation of lipoxygenase and as such possess therapeutic value in the treatment of inflammatory conditions and allergic responses such as anaphlaxis and asthma.

Lipoxygenases in mammals have been found in the lung, platelets, and white cells. They are enzymes capable of oxidizing arachidonic acid into hydroperoxyeicosatetraenoic acids (HPETEs) and their stable products hydroxyeicosatetraenoic acids (HETEs). Lipoxygeneases are classified according to the position in the arachidonic acid which is oxygenated. Platelets metabolize arachidonic acid to 12-HETE, while polymorphonuclear leukocytes contain 5 and 15 lipoxygenases. It is known that 12-HETE and 5, 12-diHETE are chemotactic for human neutrophils and eosinophils, and may augment the inflammation process. 5-HPETE is known to be a precursor of slow-reacting substance of anaphylaxis (SRS-A). The SRS family of molecules, such as leukotrienes B, C, and D, have been shown to be potent bronchoconstrictors (see, NATURE 288, 484-486 (1980)).

The following protocol describes an assay to detect inhibitors of the lipoxygenase pathway. Such inhibitors are believed to be capable of modulating the biosynthesis of the leukotrienes, a property believed to be useful in treating asthma and inflammatory disease states.

Protocol for Detecting Inhibitors of the Lipoxygenase Pathway

A suspension of rat neutrophils in buffer is incubated for 3 minutes at 30° C. with [$^{14}$C]-arachidonic acid (AA) and Calcium Ionophore A23187. Citric acid (2M) is used to quench the reaction. Following the addition of a trace amount of ($^3$H)-5-HETE together with an excess of unlabeled 5-HETE to each tube, the mixture is extracted with chloroform/methanol. The organic layer is washed with dilute acid and an aliquot is transferred to glass tubes and dried. The residue is dissolved in a small volume of chloroform and an aliquot is spotted on silica gel TLC sheets, which are developed with an ethyl acetate/isooctane/water acetic acid solvent system. The 5-HETE spots are visualized with iodine, cut out and placed in scintillation vials for counting. After adjusting for the extraction efficiency, the amount (pmole) of [$^{14}$C]-5-HETE in each of the tubes is quantitated. The net pmoles of 5-HETE are obtained by subtracting the pmoles of 5-HETE in the tubes containing buffer alone (blank) from the pmoles of 5-HETE in the tubes containing buffer and cells (control). The ability of the test compounds to modulate the activity of this enzyme is determined by a decrease or increase in the net amount of 5-HETE produced.

1,6-Bis-[N-(2-imidazolino)-4-aminophenyl]hexane on such testing indicated a value, $I_{50}=1.7$ $\mu$M illustrating potent inhibiting activity of the present new compounds.

Some compounds in this invention also display potent activities in regulating phospholipases and as such possess therapeutic value in the treatment of inflammatory conditions.

Inflammatory responses to a variety of offending stimuli are promoted by products of arachidonic acid metabolism. These products include leukotrienes (SRS-A), prostaglandins, prostacyclin and its metabolites, and thromboxanes. No matter what combination of products results from passage of substrate down the branches of this complex cascade, the initial step involves the release of arachidonic acid from phospholipids or from triglycerides containing this long-chain fatty-acid. The enzymes catalyzing such release of arachidonic acid are: (a) phospholipase C followed by diglyceride lipase; (b) phospholipase A$_2$, either soluble or membrane-bound; and (c) a lipase able to degrade triglycerides that contain arachidonic acid.

An assay has been developed to test the ability of the invented compounds on the activity of the phospholipases. In this protocol, a procedure is described for testing the inhibitory effects of these compounds of phospholipase C (PLC).

Protocol for In Vitro Assay for Inhibitors of Phospholipase

The PLC employed in this screen is obtained by aggregation of purified rat platelets in the presence of CaCl$_2$ and ADP. In the enzyme assay, phosphatidylinositol having $^3$H-labeled arachidonate residues at R2 is employed as substrate. PLC acts by cleaving the phosphate ester bond yielding diglyceride as follows:

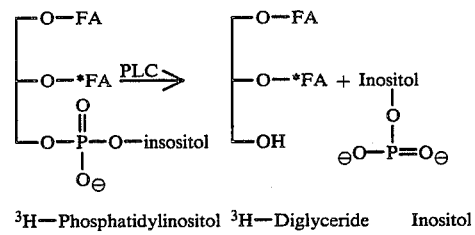

$^3$H—Phosphatidylinositol    $^3$H—Diglyceride    Inositol

Following completion of the reaction, the assay medium is acidified and extracted with hexane which takes up unreacted substrate and diglyceride. The hexane extract is passed over a short silica gel column which retains 99% of the phosphatidylinositol. The $^3$H-labeled diglyceride is not retained (95% recovery in eluate) and is collected directly in scintillation counting vials. The diglyceride is conveniently quantitated by liquid scintillation spectrometry.

The compounds were tested at 300 $\mu$M in a buffer containing 0.06 mM unlabeled phosphatidylcholine (PC), 20–30,000 cpm of $^{14}$C [PC], 150 mM NaCl, 5 mM CaCl$_2$ and 50 mM Tris(hydroxymethyl)methylaminopropanesulfonic acid buffer, adjusted to pH 9.0 with 1N NaOH. The temperature of the buffer is maintained at a temperature of 37° C. The reaction was initiated by addition of the enzyme and it was terminated 10 minutes later by addition of 1 ml of 1N HCl.

Following acidification, the samples were extracted with 2 ml of isopropyl alcohol and 2 ml of hexane, vortexed and allowed to stand until the phrases separate. Free inositol and unreacted substrate were taken up in the isopropanol-saturated hexane. The hexane phase of the extraction mixture was transferred to a short silica gel column which retained unreacted phosphatidylinositol, but not the ³H-diglyceride. The column effluent was collected directly in scintillation vials. The columns were washed once with additional 2 ml of hexane. The radiolabeled diglycerides were quantitated by liquid scintillation spectrometry.

1,6-Bis-[N=(2-imidazolino)-4-aminophenyl]hexane on such testing indicated a value of $I_{50}=14$ μM illustrating potent activity of the present new compounds.

What is claimed is:

1. A compound of the formula

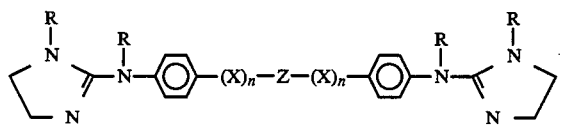

or pharmaceutically acceptable salt thereof; wherein:
Z is an unsubstituted normal alkylene chain of up to 8 carbon atoms or a substituted normal alkylene chain in which the substituent is lower alkyl, phenyl or benzyl of up to 8 carbon atoms in the normal chain and up to a total of about 12 carbon atoms;
X=O or S;
n=0 or 1;
each R is H, lower alkyl or lower alkanoyl; and
the phenyl groups separated by —(X)n—Z—(X)n— may optionally be substituted by methyl or chloro.

2. The compound according to claim 1 wherein each R is hydrogen, X=O and n=1.

3. The compound according to claim 2 wherein Z is alkylene containing from 4 to 6 carbon atoms in the principal chain.

4. The compound according to claim 1 which is 1,4-bis-[4-(N-(2-imidazolino)amino)phenoxy]-butane.

5. The compound according to claim 1 which is 1,4-bis-(4-(N-(2-imidazolino)amino)phenyl)-2,3-dimethylbutane.

6. The compound according to claim 1 which is 1,6-bis-(3-methyl-4-(N-(2-imidazolino)amino)phenyl)hexane.

7. The compound according to claim 1 which is 1,6-bis(3-chloro-4-(N-(2-imidazolino)amino)phenyl)hexane.

8. The compound according to claim 1 which is 1,5-bis(4-(N-(2-imidazolino)amino)phenyl)pentane.

9. The compound according to claim 1 which is 1,5-bis(4-(N-(2-imidazolino)amino)phenyl)3-benzylpentane.

10. The compound according to claim 1 which is 1,6-bis(4-(N-(2-(1-acetyl)imidazolino)amino)phenyl)-hexane.

11. The compound according to claim 1 which is 1,6-bis(4-(N-(2-imidazolino)amino)phenyl)hexane.

12. A compound according to claim 1 wherein n=0.

13. An anti-inflammatory composition comprising an anti-inflammatory effective amount of compound according to claim 1 and a pharmaceutical carrier therefor.

* * * * *